United States Patent [19]

Sugisaki et al.

[11] Patent Number: 4,827,970

[45] Date of Patent: May 9, 1989

[54] DEVICE FOR CONTROLLING LIQUID DROPPING

[75] Inventors: Yuzuru Sugisaki; Makoto Takada; Kazuhiko Tokuda, all of Shizuoka; Yasuo Suzuki, Yokohama; Takashi Oya, Sagamihara; Shoichi Tomeba, Sagamihara; Shinichiro Yoshida, Sagamihara, all of Japan

[73] Assignee: Kawasumi Laboratories, Inc., Tokyo, Japan

[21] Appl. No.: 108,477

[22] Filed: Oct. 13, 1987

[30] Foreign Application Priority Data

Dec. 18, 1986 [JP] Japan ................................ 61-299944
Dec. 18, 1986 [JP] Japan ........................... 61-193759[U]

[51] Int. Cl.$^4$ ............................................. A61M 5/00
[52] U.S. Cl. .................................. 137/486; 137/487.5; 604/250; 604/253
[58] Field of Search ................. 604/65, 67, 250, 251, 604/253; 137/486, 487.5

[56] References Cited

U.S. PATENT DOCUMENTS

| | | | |
|---|---|---|---|
| 3,450,153 | 6/1969 | Hildebrandt | 137/486 |
| 3,601,124 | 8/1971 | Petree | 137/486 X |
| 4,137,940 | 2/1979 | Faisandier | 137/486 |
| 4,452,273 | 6/1984 | Hanzawa | 60/253 |

Primary Examiner—Alan Cohan
Attorney, Agent, or Firm—Michael J. Striker

[57] ABSTRACT

A liquid dropping control device holds a bendable tube between a stationary klemmen and a movable klemmen, and adjusts a throttling amount of the tube by the movable klemmen, and comprises a means for detecting dropping of a liquid staying in a dropping tube, to be connected to said tube; a means for moving at high speed the movable klemmen to a direction of opening said tube so as to rapidly start dropping of the liquid staying in the dropping tube; a means for, after detecting start of the liquid dropping, moving the movable klemmen in a direction of throttling the tube and stopping it; and a means for, after detecting subsequent droppings, moving the movable klemmen at low speed so as to control said subsequent droppings at a determined speed.

8 Claims, 4 Drawing Sheets

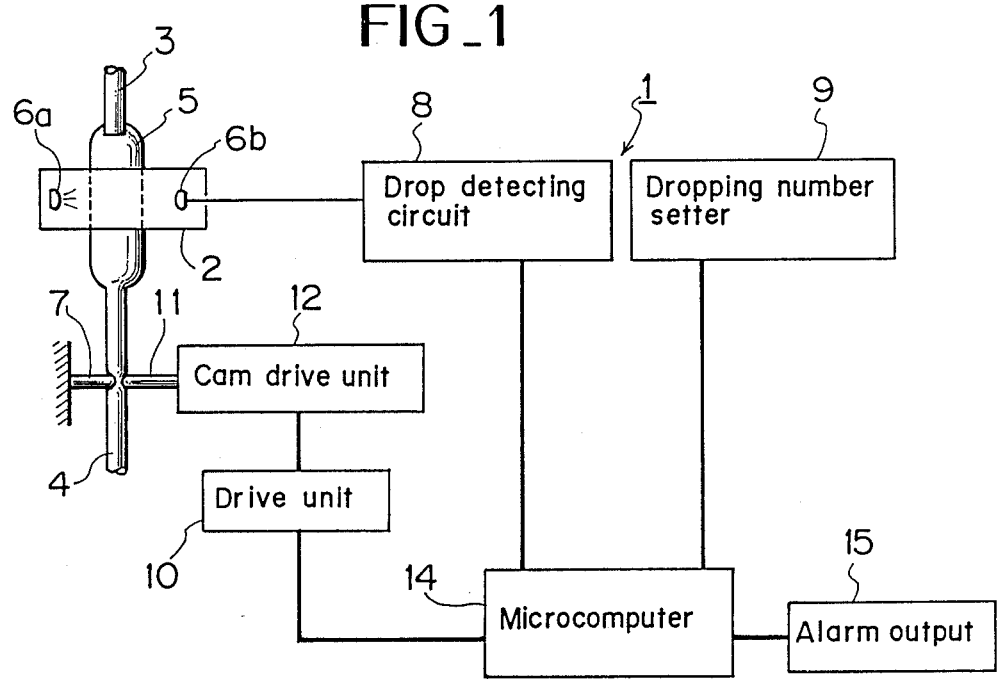
FIG_1
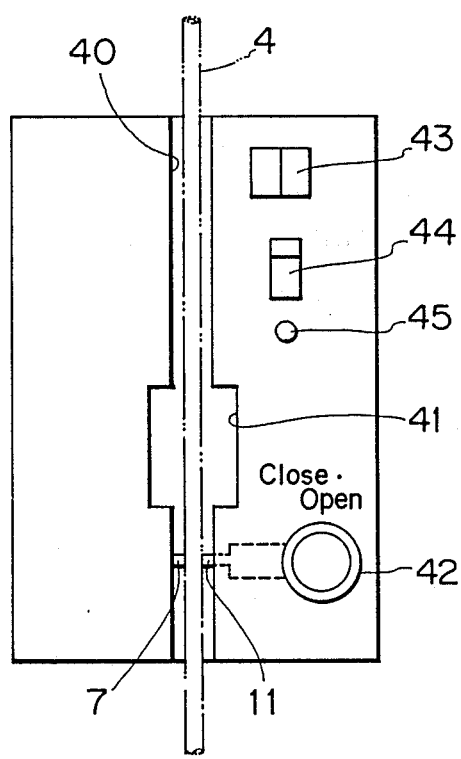
FIG_6
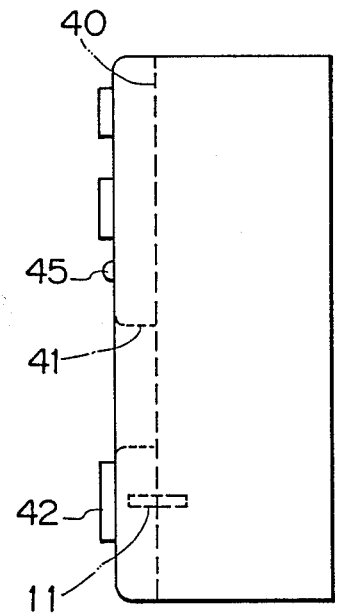
FIG_7

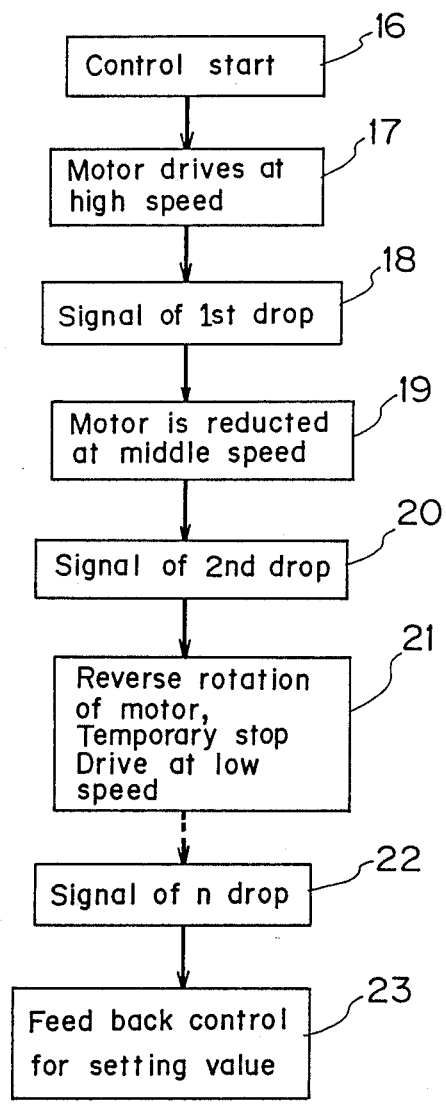
FIG_2
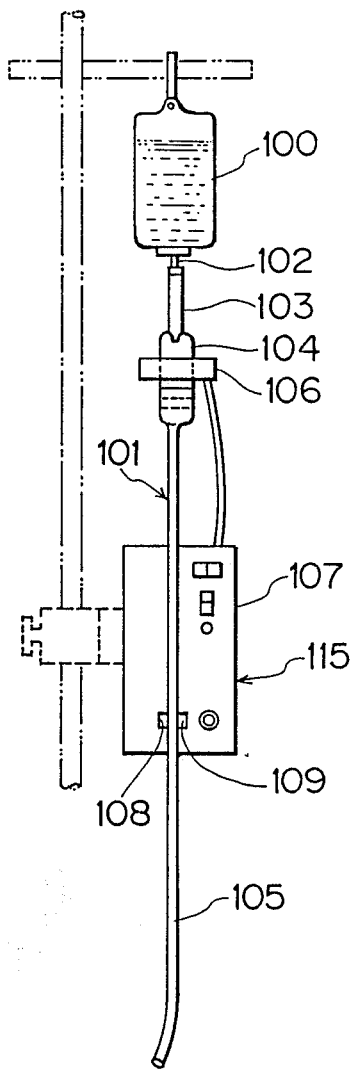
FIG_8
(PRIOR ART)

FIG_3
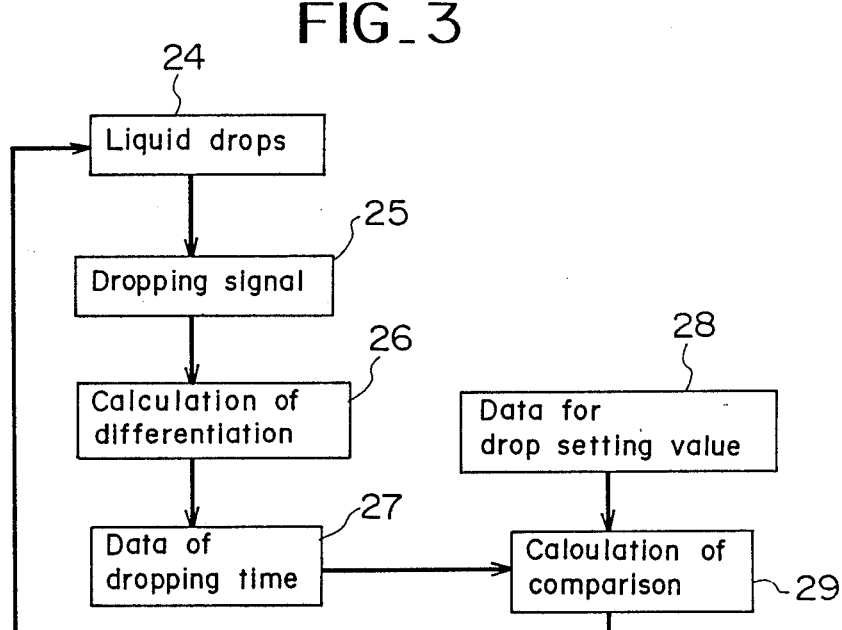
FIG_9 (PRIOR ART)
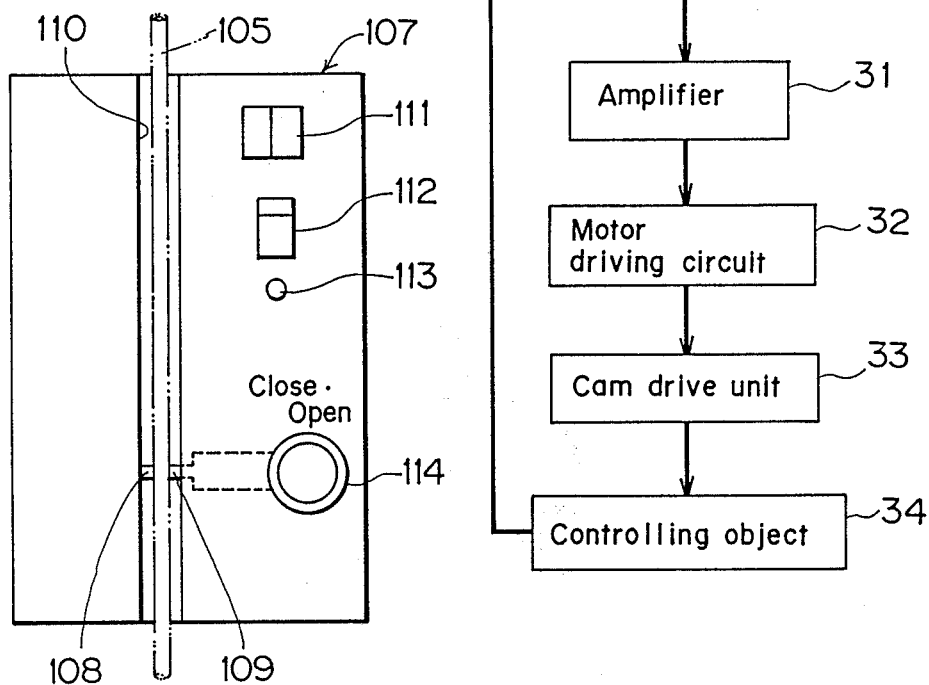

FIG_4
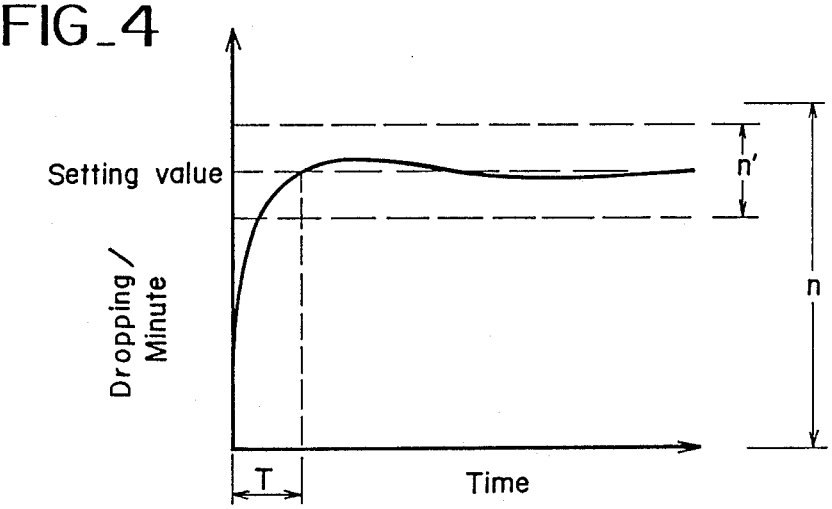
FIG_5
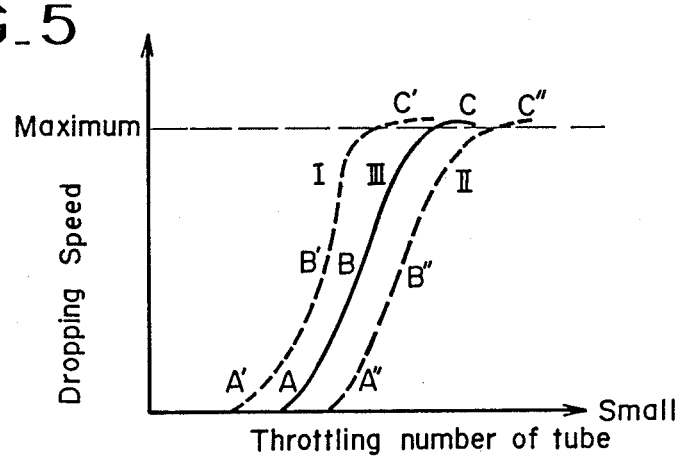
FIG_10 (PRIOR ART)
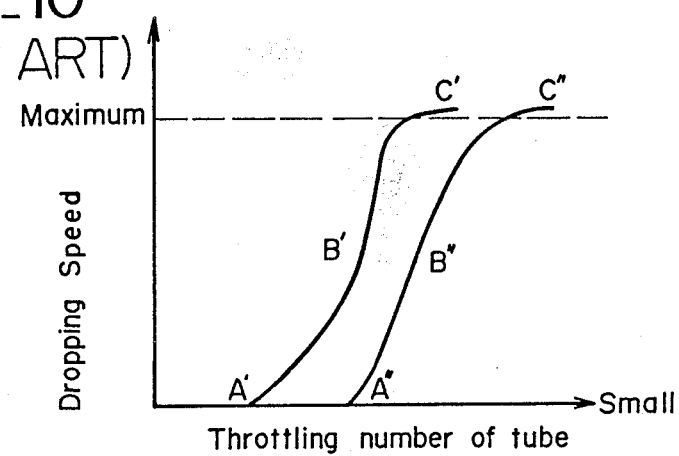

DEVICE FOR CONTROLLING LIQUID DROPPING

BACKGROUND OF THE INVENTION 1. (Field of the invention)

The present invention relates to a device which controls dropping at a desired speed of, for example, a medical liquid to be injected into a interior of a living body via 1 liquid sending set.

2. (Description of the prior art)

Medical liquid supported in a container is injected into the interior of a patient's body through a liquid sending set. and the dropping speed of the medical liquid must be controlled appropriately.

A manual roll clamp has been conveniently used as the dropping speed control. However, since the dropping speed is changed as a time passes and the roll has to be adjusted each time, a device which automatically controls the dropping speed has been recently distributed.

FIG. 8 is an outlined view showing a liquid sending control device now in use, where a container 100 holds the liquid, and a liquid carrying set 101 introduces the medical liquid into the interior of the patient's body. The liquid sending set 101 comprises a liquid needle 102 to be pierced into a mouth part of the container, a dropping tube 104, bendable tubes 103, 105 to be connected to the upper and lower parts of the dropping tube 104, and an injection needle (not shown) to be connected to the lower tube 105.

A liquid carrying control device 115 is composed of a dropping sensor 106 to be attached to the dropping tube 104 and a control device 107.

The control device 107 is, as shown in FIG. 9, formed with a tube holding groove 110 centrally in a vertical direction, and provided with a stationary clamp 108 and a movable clamp 109 in opposition to each other at a lower part of the tube holding groove 110.

A dropping number set switch 111 an electric source switch 112, an alarm lamp 113, and a thumb 114 for opening or closing the movable clamp 109 when the tube 105 is attached into or detached from the groove 110 are shown.

Such a foregoing device detects the dropping number of the medical liquid into the dropping tube 104 with the dropping sensor 106, calculates it into a dropping speed per unit time by a calculation device installed in the control device 107, moves a clamp 109 at constant speed so as to provide a predetermined dropping speed, and automatically controls a throttling amount of the tube 105.

However, since the liquid carrying control device only moves the clamp 109 at the constant speed for controlling the throttling amount of the tube 105, it is difficult to bring the dropping speed to a determined dropping number rapidly and stably when starting to send the liquid, despite resilience and recovery of the bendable tube 105. This will be explained with reference to FIG. 10.

FIG. 10 is a characteristic view showing the relationship between the throttling amount of the bendable tube 105 and the liquid dropping number, where A' - B' - C' and A" - B" - C" are S curves proper for two kinds of liquid sending sets, and A' and A" are landing points of 1st drops, and B' and B" are close to the determined values, and C' and C" are landing points of the maximum drops.

As is apparent from the same, with respect to the bendable tube 105 held between the stationary clamp 108 and the movable clamp 109, an opening area of the tube 105 is not proportional to the liquid flowing amount, and the dropping number is rapidly changed around A', A" and B', B" by slightly changing the throttling amount. Therefore, when the clamp 109 is moved at a certain speed, it is difficult to bring the throttling amount nearly to the determined value.

For example, if the movable clamp 109 is moved at the high speed for starting to send the liquid earlier, said changing of the dropping number exceeds a large range, and when the movable clamp 109 is returned at high sped to compensate for this exceeding, this return will overrun.

If the clamp 109 is moved at a determined high speed, it is difficult to converge the dropping number nearly to the determined values B', B", and the dropping number is made unstable.

If the clamp 109 is moved to the determined low speed for cancelling unstability, it takes much time (starting time for sending the liquid) to move the clamp 109 from a zero position (the position where the tube is completely closed) to the position of the first dropping.

Further, if the clamp 109 is moved at the determined middle speed, there occurs a defect involved with any one of the high speed movement and the low speed movement.

On the other hand, when the bendable tube 105 is attached to the control device 107 and since the tube 105 is inserted successively in the length of the narrow groove 110, the attachment is troublesome. Beside, the tube 105 is pressed in the groove 110 under pressure, so that the tube is loaded over a full length, and a portion about half way become twisted or caused with strain, and the medical liquid does not flow smoothly.

SUMMARY OF THE INVENTION

It is an object of the invention to provide a device which may control the movable clamp, where the throttling amount of the bendable tube is changed by moving the clamp so a to control the liquid dropping speed by starting the liquid dropping in a short time, and the bringing the dropping speed gradually to the determined speed, so that the dropping speed is made stable.

It is another object of the invention to provide a device which is of high safety, where the movable clamp closes the bendable tube at an abnormal case of the dropping speed so as not to inject excessive liquid into the interior of the body.

It is a further object of the invention to provide a device which is of high efficiency and high safety, where a micro computer is employed to simplify a control part and a mechanism part.

It is a still further object of the invention to provide a device to which the bendable tube is easily attached without causing twisting, strain or load, and the liquid within the tube flows smoothly.

The above mentioned objects may be accomplished by device mentioned below.

The device is that the bendable tube is held between the stationary clamp and the movable clamp, the throttling amount is controlled by the movable clamp to adjust the liquid dropping speed. The device comprises a means for detecting dropping of a liquid into a dropping tube, to be connected to said tube; a means for moving at high speed the movable clamp to a direction of opening said tube so as to rapidly start dropping of the liquid in the dropping tube; a means for, after detecting start of the liquid dropping, moving the movable clamp in a direction of throttling the tube and stopping it; and a means for, after detecting subsequent droppings, moving the movable clamp at low speed so as to control said subsequent droppings at a determined speed.

BRIEF DESCRIPTION OF THE DRAWINGS

FIG. 1 is a block diagram exemplifying a liquid dropping control device according to the invention;

FIG. 2 is a flow chart showing a method of controlling the liquid dropping by the invention;

FIG. 3 is a block diagram explaining actuation of a micro computer of the invention;

FIG. 4 is a characteristic view showing changes of the dropping number as time passes in the invention;

FIG. 5 is a characteristic view showing a relationship between the dropping number and the throttling amount of the tube according to the invention;

FIG. 6 is a front view of a control device of the invention;

FIG. 7 is a side view of the above control device;

FIG. 8 is an outlined view showing use of a conventional liquid dropping control device;

FIG. 9 is a front view of the above conventional device; and

FIG. 10 is a characteristic view showing a relation between the throttling amount of an ordinary bendable tube and the dropping number.

DESCRIPTION OF THE PREFERRED EMBODIMENT OF THE INVENTION

An embodiment of the invention will be explained with reference to the attached drawings.

FIG. 1 is a block diagram exemplifying a liquid dropping control device of the invention.

In the same, a dropping tube 5 constitutes one part of a liquid sending set. A bendable tube 3 is connected to an upper part of the dropping tube 5. A bendable tube 4 is connected to the lower part of the dropping tube 5. Although not shown, the upper tube 3 is connected with a liquid needle to be pierced into a mouth part of a medical liquid container, and the lower tube 4 is connected with an injection needle to be pierced into a patient at a blood vessel. The droping tube 5 and the tubes 3, 4 are made of permeable or semi permeable vinyl chloride.

The present invention is a device which controls the dropping speed of the medical liquid flowing in the liquid sending set as shown by an entire body 1.

A liquid dropping sensor 2 is to be detachably attached to the dropping tube 5 where a luminous diode 6a and a light receiving diode 6b are installed. When the liquid drops into the dropping tube 5 from the upper tube 3, the dropping liquid interrupts a light path of the diodes 6a, 6b, and a liquid drop detecting circuit 8 then detects a change of light amount, and a signal is input into a microcomputer 14.

A stationary clamp (clamp) 7 and a movable clamp (clamp) 11 in opposition, are shown. The lower bendable tube 4 is held by these clamps. If the clamp 11 is moved to change the throttling amount of the tube 4, the dropping speed of the liquid in the dropping tube 5 is adjusted.

A cam drive unit 12 moves the clamp 11, which is composed of a drive motor, cams and gears.

A drive unit 10 responds to a signal from the micro computer 14, and sends the signal to a drive motor of the clamp 11, and controls the rotation speed and direction of the drive motor.

A dropping number setter a inputs a required dropping speed to the microcomputer 14.

An alarm output 15 detects abnormal dropping speed and other problems, or sends the alarm output signal to the drive circuit 10 of the cam drive unit 12, so that the clamp 11 is moved at the high speed in the throttling direction to stop sending of the medical liquid.

FIG. 2 is a flow chart of the liquid dropping control system by the microcomputer 14.

The motor of the cam drive unit 12 is reversed by the signal from the control start 16 of the device 1, and the clamp 11 moves and presses the bendable tube 4 to the stationary clamp 7, and the tube 4 is perfectly closed (called as "control starting point" hereinafter).

Then, the motor is rotated forward at high speed 17, and the klemmen 11 moves at the high speed 17 the bendable tube 4 in the opening direction, and a first drop in the dropping tube 5 is made rapidly.

The drop detecting circuit 8 detects the first drop as a dropping signal 18, and the motor speed is reduced 19 to the middle speed so that the movable clamp 11 is reduced in movement.

After detecting a dropping signal 20 of a second drop, the motor is reversed in a moment, and the clamp 11 is slightly moved in a throttling direction of the tube 4, and the rotation of the motor is stopped temporarily, so that the movement of the clamp 11 is stopped 21 (called as "drop starting point" hereinafter). This is because dropping of the medical liquid of the first drop is rapidly induced, and an overopening of the tube 4 is slightly revised when the clamp 11 is moved to the opening direction at the maximum speed. Taking into consideration the resiliency and recovery of the bendable tube, attention is paid to a responding ability in shaping at the held portion of the bendable tube 4 by moving of the clamp 11.

When the dropping signal 22 of an n drop is detected, the motor is rotated at the low speed (shown with "21"), and while the clamp 11 is moved at the low speed in the opening or throttling direction of the bendable tube 11, it is moved to a feedback control 23 to a determined value.

FIG. 3 shows a block diagram of the feedback control 23.

A dropping signal 25 of the drop 24 of the n drop is input into a differentiation circuit 26, and after a dropping time data 27 is calculated, the signal 25 is input into a comparison calculating circuit 29. This circuit 29 has been input with data 28 for a drop set value, and after a comparison is made with the dropping time data 27, an output signal therefrom is input into the motor drive circuit 32 via the differentiation circuit 30 and an amplifier circuit 31. The input signal in the motor drive circuit 32 is inverted into an output signal for driving the motor, and the rotation of the motor constituting the cam drive unit 12 is controlled. In accompany therewith, the clamp 11 is moved via the mechanisms such as cams and gears, and an object 33 (the amount of throttling the tube) to be controlled is adjusted, so that a dropping interval of n+1 is controlled. The drop of this n+1 drop is a new dropping signal 25, and subsequently the dropping speed is controlled.

FIG. 4 is a graph showing changes of the droppings as time passes when the dropping of the liquid is controlled by the present device. This graph will be apparent in comparison with the flow chart of FIG. 2. The throttling amount is the maximum at the control starting point, and the dropping number is zero. T is time until the drop starting point from rapid induction of the dropping of the 1st drop in correspondence to 17 to 21 of FIG. 2. At T, the difference between the drop determining speed and an actual dropping speed is controlled to be substantially zero, and the dropping speed is controlled not to be outside of a control area n'. n shows a control limiting scope by the present device If the dropping speed is abnormally decreased or increased, the movable clamp 11 is returned to a cancelling point of the control start, that is, 0 point at the maximum throttling, and stops the dropping.

FIG. 5 is a graph showing relationship between the tube throttling amount and the dropping speed, where A, A', A" show the drop starting points, and B, B', B" are close to the determined points, and C, C', C" show the maximum dropping number points. In the same, the curve II (A - B - C) relates to the present invention, and the curve I (A' - B' - C') and the curve II (A" - B" - C") relate to the conventional examples where are used tubes of different thicknesses and different materials. It is seen that the device of the present invention may control the dropping number within the determined control area, irrespective of the kinds of the liquid sending sets.

FIG. 6 is a front view of the present control device, and FIG. 7 is a side view of the same.

The device is centrally formed with a groove 40 for attaching the lower bendable tube 4 of the liquid sending set, the groove 40 being formed with an intermediate groove 41 of large width. The groove 41 has the same depth as the tube attaching groove 40, and its width is as large as a finger would be adapted. In FIGS. 6 and 7, a dropping number set switch 43, a switch 44 of an electric source, an alarm lamp 45, and a thumb 42 for opening and closing the movable klemmen are shown, as in the prior art.

A further reference will be made a sequential operation for attaching the bendable tube to the present device.

The thumb 42 is opened to make a clearance between the stationary klemmen 7 and the movable clamp 11, and the tube 4 is stretched by the both hands and fitted to the groove 40, and the both ends of the tube 4 are pressed to the bottom of the groove 40. The tube 4 in the intermediate groove 41 is pushed by the finger, and the upper part and the lower part of the tube than the groove 41 are separately fitted into the attaching groove 40 in the length. The lower tube is held between the stationary clamp 7 and the movable clamp 11.

The intermediate groove 41 may be positioned in any part close to both clamps 7 and 11, for example, at the lower part of them.

The above mentioned is exemplified of the present invention, and therefore, this invention is not limited to said embodiment. The invention may be utilized to not only the medical liquid control but also dropping controls of the liquid to be used in the physical and chemical experimental fields.

What is claimed is:

1. A device for controlling a liquid dropping speed of a liquid of a medical liquid sending set which has a bendable tube for leading a liquid and a dropping tube connected to the bendable tube, comprising a stationary clamp and a movable clamp for clamping the bendable tube; a device for detecting a dropping of the liquid into the dropping tube; a microcomputer for controlling operation of a drive device of the movable clamp in association with the drop detecting device, the microcomputer being provided with means for moving the movable clamp in a direction throttling the tube by a signal for starting the control, and closing the bendable tube by means of the stationary clamp and the movable clamp; means for moving at high speed the movable clamp in the direction releasing the bendable tube so as to rapidly start dropping at the closing condition of the bendable tube; means for slightly moving the movable clamp in the direction throttling the tube after having detected the first dropping, and then temporarily stopping the movable clamp; and means for feedback controlling the dropping speed into the dropping tube, while moving at low speed the movable clamp in the direction releasing or throttling the bendable tube after having detected a dropping subsequent to the first dropping.

2. The device as claimed in claim 1, further comprising means for rapidly closing the bendable tube by the movable clamp when the dropping speed is abnormal, and issuing an alarm output.

3. The device as claimed in claim 1, further comprising
means for calculating a dropping signal from the detecting means by differentiation;
means for comparing liquid dropping time data and dropping determined data; and
means for moving the movable clamp to provide a liquid dropping determined value in response to a signal from the comparison calculation so as to adjust the throttling amount of the bendable tube.

4. The device as claimed in claim 1, wherein the detecting means includes a liquid dropping sensor for detecting dropping of the liquid into the dropping tube, a liquid drop detecting circuit, and a dropping number setting circuit; and further comprising:
a drive circuit connectable with a drive unit of the movable clamp;
a microcomputer connected to each of said circuits;
means for causing the microcomputer to issue a high speed control signal and for moving the movable clamp at high speed in a direction for releasing the bendable tube and to generate a first drop from zero drop;
means for transmitting said control signal as a drive signal through the microcomputer, after having detected a second drop from the drop detecting circuit, and for moving the movable clamp in a direction for slightly throttling the bendable tube and stopping said movable clamp; and
means for causing the microcomputer to issue a low speed control signal from a third drop to an nth drop and for moving the movable clamp in a direction for releasing the bendable tube.

5. A method of controlling a liquid dropping speed of a liquid of a medical liquid sending set which has a bendable tube for leading a liquid and a dropping tube connected the the bendable tube, the method comprising providing a stationary clamp and a movable clamp for clamping the bendable tube; detecting a dropping of the liquid into a dropping tube; controlling by a microcomputer operation of a drive device of the movable clamp in association with the drop detecting device, including moving the movable clamp in a direction throttling the tube by a signal for starting the control, and closing the bendable tube by means of the stationary clamp and the movable clamp; moving at high speed the movable clamp in the direction releasing the bendable tube so as to rapidly start dropping at the closing condition of the bendable tube; slightly moving the movable clamp in the direction throttling the tube after having detected the first dropping, and then temporarily stopping the movable clamp; and feedback controlling the dropping speed into the dropping tube while moving at low speed the movable clamp in the direction releasing or throttling the bendable tube after having detected a dropping subsequent to the first dropping.

6. The method as defined in claim 5; further comprising:
   rapidly closing the bendable tube by the movable clamp when the dropping speed is abnormal; and
   issuing an alarm output when the dropping speed is abnormal.

7. The method as defined in claim 5; and further comprising:
   calculating a dropping signal from the detecting by differentiation;
   comparing the liquid dropping time data and dropping determined data; and
   moving the movable clamp to provide a liquid dropping determined value in response to a signal from the comparing so as to adjust the throttling amount of the bendable tube.

8. The method as defined in claim 5, wherein the detecting includes detecting with a liquid dropping sensor, a liquid drop detecting circuit, and a dropping number setting circuit; further comprising:
   driving a drive unit of the movable clamp with a drive circuit;
   causing a microcomputer connected to each of the circuits to issue a high speed control signal;
   moving the movable clamp at high speed in a direction for releasing the bendable tube so as to generate a first drop from zero drop;
   transmitting the high speed control signal as a drive signal thorugh the microcomputer after having detected a second drop from the drop detecting circuit;
   moving the movable clamp in a direction for slightly throttling the bendable tube and stopping the movable clamp;
   causing the microcomputer to issue a low speed control signal from a third drop to an nth drop; and
   moving the movable clamp in a direction for releasing the bendable tube.

* * * * *